United States Patent
Koftis et al.

(10) Patent No.: US 11,046,810 B2
(45) Date of Patent: Jun. 29, 2021

(54) PROCESS FOR PREPARING BIODEGRADABLE POLYMERS OF HIGH MOLECULAR WEIGHT

(71) Applicant: PHARMATHEN S.A., Pallini-Attikis (GR)

(72) Inventors: V. Theocharis Koftis, Salonika (GR); Efstratios Neokosmidis, Salonika (GR); Konstantina Karidi, Salonika (GR); Anastasia-Aikaterini Varvogli, Salonika (GR)

(73) Assignee: PHARMATHEN S.A., Attikis (GR)

( * ) Notice: Subject to any disclaimer, the term of this patent is extended or adjusted under 35 U.S.C. 154(b) by 147 days.

(21) Appl. No.: 16/471,918

(22) PCT Filed: Dec. 21, 2017

(86) PCT No.: PCT/EP2017/025369
§ 371 (c)(1),
(2) Date: Jun. 20, 2019

(87) PCT Pub. No.: WO2018/127270
PCT Pub. Date: Jul. 12, 2018

(65) Prior Publication Data
US 2019/0315913 A1  Oct. 17, 2019

(30) Foreign Application Priority Data

Jan. 4, 2017 (EP) .................. PCT/EP2017/025000

(51) Int. Cl.
*C08G 63/08* (2006.01)
*A61K 47/34* (2017.01)
*C08G 63/81* (2006.01)
*C08G 63/85* (2006.01)

(52) U.S. Cl.
CPC .............. *C08G 63/08* (2013.01); *A61K 47/34* (2013.01); *C08G 63/81* (2013.01); *C08G 63/85* (2013.01)

(58) Field of Classification Search
USPC ........ 528/271, 272, 279, 354; 424/400, 426, 424/450, 501; 428/411.1, 412; 514/1.1, 514/249, 451, 464
See application file for complete search history.

(56) References Cited

U.S. PATENT DOCUMENTS 6,372,880 B1 * 4/2002 Shinoda .............. A61K 9/1641
                                                    424/451
2009/0088835 A1  4/2009 Wang

FOREIGN PATENT DOCUMENTS

| CN | 101632834 A  | 1/2010 |
| GB | 1040168 A    | 8/1966 |
| KR | 20160126117 A| 11/2016|

* cited by examiner

*Primary Examiner* — Terressa Boykin
(74) *Attorney, Agent, or Firm* — AKC Patents, LLC; Aliki K. Collins

(57) ABSTRACT

A novel method for the preparation of biodegradable polymers is disclosed. The method produces polymers of high molecular weight and particularly allows for stirring throughout the polymerization reaction.

12 Claims, No Drawings

PROCESS FOR PREPARING BIODEGRADABLE POLYMERS OF HIGH MOLECULAR WEIGHT

TECHNICAL FIELD OF THE INVENTION

The present invention relates to a novel process for the preparation of biodegradable polymers.

BACKGROUND OF THE INVENTION

Biodegradable polymers are a continuously growing research field, due to their broad range of industrial applications. Of particular interest are biodegradable polyesters and more specifically polyesters of lactic acid, glycolic acid and their copolymers (PLGA).

The biodegradation of the aliphatic polyesters occurs by bulk erosion. The lactide/glycolide polymer chains are cleaved by hydrolysis to the monomeric lactic acid and glycolic acid which gets eliminated from the body by metabolism and exhaled as carbon dioxide and water through the Krebs cycle. It should be emphasized that these degradation products are generally considered nontoxic to living organisms. In fact lactic acid occurs naturally through metabolic activity in the human body. Due to all these properties biodegradable polyesters have found important biomedical applications as surgical sutures, implants and drug delivery systems.

PLGA attracts much interest in the biomedical field, due to its biocompatibility, biodegradability and favorable release kinetics. High molecular weight PLGAs are extremely useful in controlled drug delivery applications ["Synthesis, characterization, biodegradation, and drug delivery application of biodegradable lactic/glycolic acid oligomers: Part III. Drug Delivery Application", Artificial Cells, Blood Substitutes, and Biotechnology, 2004, 32(4), 575; Application of poly DL-lactic acids of varying molecular weight in drug delivery systems, *Drug Design and Delivery*, 1990, 5, 301]. Moreover, high molecular weight PLGAs are fabricated into surgical sutures and bone fixation nails and screws, where high mechanical strength is a must ["Trends in the development of bioresorbable polymers for medical applications", *J. Biomater. Appl.*, 1992, 6, 216; "Mechanical properties of biodegradable polymers and composites proposed for internal fixation of bone", *J. Appl. Biomater.*, 1990, 1, 57].

As the drug/biomolecule kinetic release is dramatically influenced by the polymeric degradation rate, polymers with a wide range of molecular weights and copolymer composition need to be addressed. The degradation time can vary from several months to several years, depending on the molecular weight and copolymer ratio. It goes without saying that the method for the preparation of the polymer has a significant effect on the application of the final product.

There are several polymerization processes for preparing biodegradable polyesters available in the art. Polycondensation of the respective acids provide relatively low-molecular weight polymers. The ring-opening polymerization (ROP) of the corresponding cyclic monomers (lactide, glycolide) provides access to higher molecular weight polymers. This process has also more value from technical point of view, primarily because there is no necessity for removing water from the polymerization mass, which is a by-product of the acid polycondensation.

The ROP mechanism requires the presence of an initiator, the nature of which depends on the type of the ROP. Organometallic derivatives of metals, enzymes, supported-metal catalysts and simple organic molecules have been used to this end (*Adv. Drug Delivery Rev.* 2008, 60, 1056). The most common types include metal salts, metal alkoxides, metal carboxylates and metal complexes. By careful selection of metal and ligands, reactions can be directed towards a desired polymer structure.

Depending on the nature of the initiator, the latter may require to be activated in situ with a hydroxyl containing compound (co-initiator). This is the case when, for example, the mechanism proceeds via the formation of an alkoxide ("Synthesis of polylactides in the presence of co-initiators with different numbers of hydroxyl groups", *Polymer*, 2001, 42,7541-7549). The co-initiator controls the molecular weight of the polymer by means of its ratio and its structure (mono-, di- or poly-hydroxyl containing compound). It also affects its physical properties.

The ROP method can be performed with or without a solvent. However the vast majority of the prior art produces biodegradable polymers by performing ROP without using a solvent (bulk polymerization). Of course the absence of a solvent implies a simplification of the process from a technical point of view, because no need to remove the solvent exists in that case. Arguably, though, in the absence of solvent different kinds of other practical issues.

One of them is the poor heat transfer through the polymer mass, which makes the removal of heat very challenging. Additionally, it causes large temperature gradients which are responsible for inhomogeneity in the final product. This is a very serious defect, especially for products which are meant for medical or surgical applications.

Another issue is the compatibility of the bulk method with stirred reactors. As the polymerization proceeds, viscosity rises, hence stiffing is not an actual option. The product solidifies, taking the shape of the reactor and is removed as a compact block by means of extrusion. Clearly, this is a major drawback in view of the large scales required for industrial purposes.

U.S. Pat. No. 6,706,854 attempts to solve this problem by splitting the reaction mass into smaller-volume containers. According to the method of this patent, lactide and glycolide are initially mixed in a stirred reactor and are subsequently transferred into a number of smaller-volume containers (plastic bottles), where they are polymerized under bulk conditions. While the stirring issue seems to have been somewhat addressed this way, there is still an actual barrier to the scale of the polymerization reaction, defined by the volumes of the multiple containers, instead of the volume of a single reactor. In addition, the suggested solution is both ergonomically and spatially disadvantageous.

On the other hand, polymerization in the presence of a solvent allows better control of the polymerization reaction, temperature of the polymerization mass avoiding hot spots, degradation, impurities and better mixing. It does require, though, longer reaction time, which is another feature to be avoided in the industry.

Miranda et al (*Materials research* 2015, Sup.2, 18, 200-204) perform solution polymerization for the preparation of a copolymer of poly-L-lactic acid and polycaprolactone in toluene at 120° C. The polymerization catalyst is stannous octanoate and the co-initiator used is methanol and the polymerization reaction duration was 24 hours. The polymers obtained exhibited Mn ranging from 2100 to 28900 Da which is very low for use in drug delivery systems and other applications, discussed above.

A. Meduri, T. Fuoco, M. Lamberti, C. Pellecchia, D. Pappalardo in *Macromolecules* 2014, 47, 534 prepare PLGA polymers in xylenes with aluminum catalyst synthesized as part of the project. According to the method disclosed therein, stannous octanoate, suffers from scarce reproducibility of polymerization results and the produced polymers have properties which vary from batch to batch. While those issues seem to have been addressed, the method presented therein results in Mn=4000-27000 Da. Similarly, as above, this molecular weight range is fairly low.

From the above it is evident that there is a need for a polymerization method for the production of biodegradable polymers which overcomes the technical issues caused by the bulk polymerization (lack of stirring and homogeneity, solidification within the course of the reaction, poor heat transfer and thermal control) and does not entail the drawbacks of using a solvent (longer reaction time, low molecular weight).

SUMMARY OF THE INVENTION

The present invention provides for a polymerization method of mixtures of lactide and glycolide, wherein a step of said method comprises polymerization under stirring in the presence of an organic solvent, a metal catalyst and optionally a co-initiator, wherein the polymerization is performed in a closed system.

The method of the present invention overcomes major drawbacks of prior art, which originate from mechanical properties of the polymers, while at the same time retains the characteristics of a relatively quick process, suitable for industrial applicability.

DEFINITIONS

The following terms shall have, for the purposes of this application, including the claims appended hereto, the respective meanings set forth below. It should be understood that when reference herein is made to a general term, one skilled in the field may make appropriate selections for such reagents from those given in the definitions below, as well as from additional reagents recited in the specification that follows, or from those found in literature references in the field.

Solutions are, in a limited sense, homogeneous liquid phases consisting of more than one substance in variable ratios, when for convenience one of the substances, which is called the solvent and may itself be a mixture, is treated differently from the other substances, which are called solutes (C. Reichardt, *Solvents and Solvent Effects in Organic Chemistry*, 2006, 3$^{rd}$ Edition, ISBN 3-527-30618-8).

The number-averaged molecular weight (Mn) is the statistical averaged molecular weight of all the polymer chains in the sample, and is defined by:

$$Mn = \Sigma NiMi^2 / \Sigma Ni$$

The weight-averaged molecular weight (Mw) is defined by:

$$Mw = \Sigma NiMi^2 / \Sigma NiMi$$

where Mi is the molecular weight of a chain and Ni is the number of chains of that molecular weight.

The polydispersity index (PDI) is used as a measure of the broadness of a molecular weight distribution of a polymer, and is defined by:

Polydispersity index=Mw/Mn

The inherent viscosity ($\eta_{inh}$) is used as an alternative expression of the molecular weight of the polymers, and is defined by:

$$\eta_{inh} = \ln \eta_r / c$$

where $\eta_r$ is the relative viscosity, which is defined by $t/t_0$ wherein t is the efflux time of the polymer solution and $t_0$ is the efflux time of the solvent obtained from the Ubbelohde viscometer measurement.

The intrinsic viscosity ($[\eta]$) can be also used as an alternative expression of the molecular weight of the polymers. The intrinsic viscosity is the hypothetical viscosity at a hypothetical "zero concentration".

$$\eta_{inh} = k''[\eta]^2 c + [\eta]$$

where k'' is a constant. At "zero concentration" (c=0), the y-intercept of a plot of $\eta_{inh}$ vs c equals to the intrinsic viscosity $[\eta]$.

The term "monomers", as used herein, refers to the cyclic compounds lactide and glycolide which follow the ring opening polymerization mechanism.

Metal catalyst (initiator), as used herein, refers to compounds and complexes including metallic elements that are effective as catalysts in the ring-opening polymerization and encompasses, without limitation, "transition metal catalysts".

Co-initiator, as used herein, refers to compounds which affect not only the conversion rates of the ring-opening polymerization and the polymer molecular weight, but also the properties of corresponding polymers, including degradation rate and thermal properties. Chain-length moderators are considered to be co-initiators within the scope of the present invention.

Biodegradable polymers, as used herein, refers to polymers that degrade quickly and their byproducts are eco-friendly (biocompatible) such as $CO_2$, water, methane, and inorganic compounds or biomass that is easily scavenged by microorganisms.

Additionally, it should be understood in the methods of preparation and claims herein, that the pronoun "a", when used to refer to a reagent, such as "a monomer", "a solvent" and so forth, is intended to mean "at least one" and thus, include, where suitable, single reagents as well as mixtures of reagents.

DETAILED DESCRIPTION OF THE INVENTION

It has surprisingly been found that the polymerization of mixtures of lactide and glycolide can be performed in the presence of a solvent, whereby stiffing is conveniently applied, the reaction time is limited to a few hours and the polymer product exhibits a high molecular weight, suitable for biomedical applications.

According to an embodiment of the invention, there is provided a method of polymerization of mixtures of lactide and glycolide, comprising the step of performing polymerization under stirring in the presence of an organic solvent, a metal catalyst (initiator) and optionally a co-initiator, wherein the polymerization is performed in a closed system.

Lactide, as lactic acid, exists in the form of diastereomers. Lactic acid can be L-lactic acid, D-lactic acid or D, L-lactic acid (racemate). Likewise, the lactide can be L-lactide, D-lactide, D, L-lactide (racemate) or meso-lactide.

The polymers produced according to the method of the present invention are copolymers. The skilled person understands that the method disclosed herein is not limited to a specific type of copolymer and the type which is produced may vary, depending on the conditions employed. Non-limiting examples of copolymer types are random copolymers, alternating copolymers, gradient copolymer, tapered copolymer, block copolymers.

Aprotic solvents are preferable. More preferable are aliphatic and aromatic hydrocarbons, halogenated aliphatic and aromatic hydrocarbons and aliphatic and aromatic ethers. Even more preferable are aromatic hydrocarbons and halogenated aliphatic hydrocarbons. Still more preferable is toluene and chloroform.

The presence of a solvent allows the polymerization to proceed under stirring conditions, as a consequence of the lower viscosity of the mass. Additionally, the monomers' solubility increases as the temperature rises and this dissolution phenomenon is in favor of the polymerization reaction. The presence of the solvent provides for better heat transfer and thermal control, better mixing and increased homogeneity of the polymerization mass. It also helps avoid creation of hot spots, which are responsible for heat dissipation problems and discoloration of the polymer. A further advantage is the easier manipulation of the polymerization conditions. Additives can easily be used and there is a broad range of design possibilities. Thus, various properties can be achieved and it is easier to modify the process (e.g. addition of nano-particles).

The amount of the solvent used may be tuned according to the other reaction parameters and the desired properties of the produced polymers. In a preferred embodiment, the ratio of the solvent with respect to the combined mass of the monomers is at least 1 ml per gram. More preferable are at least 2 ml per gram. Still more preferable are at least 4 ml per gram. Even more preferable are at least 8 ml per gram.

The apparatus which is used for the polymerization reaction operates as a closed system. Such an apparatus does not allow air (or other gas) exchange between the inner and the outer part of it once it is sealed. Reactors with this feature are very common in the industry as well as in most laboratories. A common type of such apparatuses are autoclaves. All these apparatuses tolerate a certain degree of internal pressure, depending on their characteristics. Accordingly, a reaction performed in such apparatuses or equipment may be performed beyond the boiling point of the solvent, as the increase of the pressure allows the solvent (or at least its major part) to remain in the liquid phase.

The temperature at which the polymerization reaction is performed depends on the desired polymerization rate and subsequently on the target molecular weight of the resulting polymer. Notably, stiffing allows a more flexible choice of temperature with respect to bulk polymerization, because the solvent dissolves, at least partially, the monomers and their melting is not a prerequisite. This is important for industrial purposes, as the higher the temperature to be reached, the more demanding and energy consuming the process is.

Surprisingly, the reaction time is considerably shorter and provides polymers of higher molecular weight compared to prior art processes which employ organic solvents.

The polymerization reaction occurs in the presence of a metal catalyst. Several catalysts and initiators have been tested in glycolide/lactide copolymerization. Early studies include the testing of commercially available chlorides, alkoxides, oxides or sulfides of main groups and transition metals (Sn, Al, Zr, Ti, Pd, Cd, and Zn).

Preferable metal catalysts are tin, zinc, aluminum. More preferable are halides, alkoxides and carboxylic acid salts of tin, zinc and aluminum. Even more preferable are tin and aluminum alkoxides and carboxylic acid salts. Even more preferable are tin alkoxides and carboxylic acid salts. Still more preferable is tin (II) 2-ethylhexanoate [$Sn(Oct)_2$].

Co-initiators suitable for the present invention are aliphatic mono-, di- or polyalcohols. Alternatively, the present method may be performed without a co-initiator, whereby any moisture may initiate the polymerization reaction. Therefore, the presence of a co-initiator is optional and depends on the sought properties of the end polymer. The skilled person understands that the type of the co-initiator has an effect to the chain length of the polymer as well as to the type of the polymer. Such types are, for example linear, branched and cross-linked polymers. Branched polymers include more specific types such as star polymers, graft polymer, dendrimers and hyperbranched polymers.

The scope of the present invention is therefore not limited to a specific type of polymer. According to the present invention, linear, branched or cross-linked polymers may be prepared, depending on the conditions employed by the skilled person.

Preferable co-initiators are mono-, di- or polyalcohols with 1-20 carbon atoms. More preferable are methanol, butanol, 1,4-butanediol, 1-dodecanol, glucose, di(trimethylopropane), pentaerythritol, glycerol. Alcohols with a single —OH group or two —OH groups are normally used for linear polymers whereas polyalcohols are used for branched-type polymers.

The feed ratio of the monomers depends on the type of the polymer that is sought to be produced and its applications and it is adjusted accordingly. The scope of the present invention, therefore embraces polymers of various composition, resulting from different ratios of the two monomers, i.e. glycolide and lactide.

The composition of PLGA is one key property which needs to be adequately controlled by the method of polymerization. It can be determined by controlling the feed ratio of the monomers. However, control of the molecular weight of PLGA, another key feature of the polymer requires extra effort. Monomer purity, catalyst concentration, polymerization temperature, polymerization time, catalyst concentration, degree of vacuum, and the amount of molecular weight controller (hydroxyl containing compound or co-initiator) added, all affect the molecular weight of the resulting polymer.

Advantageously, the method disclosed herein allows access to polymers of high molecular weight, i.e. tens or hundreds of thousands Da. This is desirable for the production of materials for a wide range of biomedical applications including drug release systems, sutures, orthopedic applications, tissue engineering, implants.

However, depending on the various factors of the reaction, the molecular weight of the resulting polymer can be adjusted as desired. The scope of the present invention, therefore embraces polymers of various molecular weights.

The molecular weight (MW) of the polymers may be measured by a variety of methods. Gel Permeation Chromatography (GPC) is employed for the determination of the molecular weight distribution of the polymers. A universal calibration curve, constructed with polystyrene standards (PolymerLabs) of known molecular weights, was employed for the determination of the MWD (Molecular Weight Distribution) of the unknown PLGA samples.

The GPC instrument can be equipped with a refractive index (RI) detector, a multi-angle laser light scattering (MALLS) detector, a viscometer detector or a combination of the above mentioned detectors.

Alternatively, the molecular weight may be measured by MS methods. A suitable mass spectrometry (MS) method for macromolecules is matrix-assisted laser desorption/ionization time-of-flight mass spectrometry (MALDI-TOF MS). This technique also provides absolution molecular weight measurement.

Alternatively, the molecular weight may be indirectly expressed as inherent/intrinsic viscosity. Inherent/intrinsic viscosity can be measured with an Ubbelohde viscometer using appropriate solvent.

In a preferred embodiment of the present invention, the Mw of the resulting polymer is at least $5\times10^3$ Da. More preferably, the molecular weight of the resulting polymer is at least $1.0\times10^4$ Da. Even more preferably, the molecular weight of the resulting polymer is at least $2.0\times10^4$ Da. Still more preferably, the molecular weight of the resulting polymer is at least $5.0\times10^4$ Da, all measured by Gel Permeation Chromatography (GPC).

It is well-known that the ring-opening polymerization of lactide and glycolide is extremely sensitive to the presence of any traces of reactive impurities and, thus, it is difficult to control its polymerization rate and molecular weight progress. Highly pure lactide and glycolide are available in the chemical industry. Alternatively, they may be purified by means of recrystallization, which is a standard purification technique well-known to the skilled person.

The polymerization rate and the molecular weight are also largely affected by the presence of water, because the latter can act both as a co-initiator as well as a chain transfer agent (CTA), lowering the molecular weight of the polymers. Hence the water content of those reaction components should be limited. Many analytical techniques, known to the skilled person, are available to this end. The Karl-Fischer method is suitable for this purpose.

The polymers prepared by the method of the present invention additionally exhibit low polydispersity index.

The method disclosed herein, furthermore, is accompanied by reproducible results. The resulting polymers show repeatable molecular weights and polydispersity index, by applying the same conditions. On the other hand, these properties have been proven to be conveniently controlled by the parameters of the method.

The biodegradable polymers produced according to the method of the present invention may be further employed in a method of production of surgical sutures, implants and drug delivery systems.

The present invention therefore also relates to a method for producing surgical sutures, implants and drug delivery systems, comprising producing a polymer with a method as disclosed herein.

The present invention preferably relates to a method for producing surgical sutures, implants and drug delivery systems, comprising producing a polymer with a method as disclosed herein.

EXAMPLES

All solvents used in the polymerization reaction were dried by means of distillation prior to their use. Monomers were purchased by commercially available sources and no further purification was required. The addition of the initiator and co-initiator solutions was carried out with the aid of flame dried glass syringes, under continuous nitrogen flushing nitrogen conditions, to ensure a strictly anhydrous environment.

Measurement of MW was performed by Gel Permeation Chromatography (GPC) as described below.

Two PLgel columns 5 μm Mixed-D 300×7.5 mm were connected in series (purchased from Agilent). The column temperature applied is 30° C. and the flow rate of the system is 1 mL/min. All samples and standards should be dissolved in Tetrahydrofuran and stirred prior to injection. The suitability of the system is evaluated by five replicate injections of the standard solution of Polystyrene MP 70000. Sample concentration is 4000 μg/mL. The chromatographic procedure includes an injection of blank solution, one injection of each of the polystyrene standards, five injections of system suitability solution, two injections of sample solution and two injections of system suitability solution as QC check (The % RSD of retention time of Polymer peak for five injections of standard solution before sample solution and for two injections of QC check after sample solution should not be more than 1% for retention time. Injection volume of all solutions is 100 μL. MW was calculated using a calibration curve, constructed with polystyrene standards (PolymerLabs) of known molecular weights (purchased from Sigma Aldrich). The calibration curve is a linear first order expression of the elution time to the log (Mw) evaluated by appropriate software.

The inherent/intrinsic viscosity of the produced polymers was measured with an Ubbelohde viscometer (Type 0c). Polymer solutions were prepared in chloroform.

Example 1

In an 9 mL autoclave vial, 0.75 g D,L-lactide (0.0052 mol) and 0.188 g (0.0016 mol) Glycolide were placed under a continuous flow of argon, followed by the addition of 0.000127 g ($6.83\times10^{-7}$ mol) 1-dodecanol (solution in toluene) and 0.000277 g ($6.83\times10^{-7}$ mol) Sn(Oct)$_2$ (solution in toluene). 4 mL of toluene was added to the autoclave vial under continuous flow of argon. The autoclave vial was then sealed under argon and immersed into a thermostated oil bath under stiffing at 160° C. After 15 hours, the polymerization reaction was stopped by quenching (i.e., by placing the flask into an ice bath). 10 ml of acetone was added in the autoclave vial to dilute the produced viscous solution under stirring overnight. The diluted solution was transferred in a round bottom flask and evaporated to dryness. The residues were dissolved in 10 ml of acetone under stirring. A sample was withdrawn in order to record a $^1$H NMR spectrum for the determination of monomers' conversion. The polymer was precipitated by addition of 100 ml of water under stirring in an ice bath. The polymer mass was isolated through vacuum filtration. The precipitated polymer was then dried under vacuum at 60° C. for 24 hours. The total monomer conversion was 97%. The inherent viscosity was 1.36 dL/g measured in chloroform at 25° C. The lactide/glycolide molar ratio determined by $^1$H NMR was 73:27. The weight averaged molecular weight was $1.60\times10^4$ Da with a polydispersity index of 1.6 as measured by gel permeation chromatography, using THF as the mobile phase and polystyrene standards.

Example 2

In an 9 mL autoclave vial, 1.5 g D,L-lactide (0.0104 mol) and 0 0.377 g (0.0033 mol) Glycolide were placed under a continuous flow of argon, followed by the addition of 0.000255 g ($1.37\times10^{-6}$ mol) 1-dodecanol (solution in toluene) and 0.00055 g ($1.37\times10^{-6}$ mol) Sn(Oct)$_2$ (solution in toluene). 4 mL of toluene was added to the autoclave vial under continuous flow of argon. The autoclave vial was then sealed under argon and immersed into a thermostated oil bath under stirring at 160° C. After 10 hours, the polymerization reaction was stopped by quenching (i.e., by placing the flask into an ice bath). 10 ml of acetone was added in the autoclave vial to dilute the produced viscous solution under stirring overnight. The diluted solution was transferred in a round bottom flask and evaporated to dryness. The residues were redissolved in 10 ml of acetone under stirring. A sample was withdrawn in order to record a $^1$H NMR spectrum for the determination of monomers' conversion. The polymer was precipitated by addition of 100 ml of water under stiffing in an ice bath. The polymer mass was isolated through vacuum filtration. The precipitated polymer was then dried under vacuum at 60° C. for 24 hours. The total monomer conversion was 98%. The inherent viscosity of this copolymer was 2.26 dL/g measured in chloroform at 25° C. The lactide/glycolide molar ratio determined by $^1$H NMR was 72:28. The weight averaged molecular weight was $2.70 \times 10^5$ Da with a polydispersity index of 1.6 as measured by gel permeation chromatography using THF as the mobile phase and polystyrene standards.

Example 3

In an 9 mL autoclave vial, 0.75 g D,L-lactide (0.0052 mol) and 0.188 g (0.0016 mol) Glycolide were placed under a continuous flow of argon, followed by the addition of 0.00064 g ($3.42 \times 10^{-6}$ mol) 1-dodecanol (solution in toluene) and 0.00028 g ($6.83 \times 10^{-7}$ mol) Sn(Oct)$_2$ (solution in toluene). 4 mL of toluene was added to the autoclave vial under continuous flow of argon. The autoclave vial was then sealed under argon and immersed into a thermostated oil bath under stirring at 160° C. After 10 hours, the polymerization reaction was stopped by quenching (i.e., by placing the flask into an ice bath). 10 ml of acetone was added in the autoclave vial to dilute the produced viscous solution under stirring overnight. The diluted solution was transferred in a round bottom flask and evaporated to dryness. The residues were dissolved in 10 ml of acetone under stirring. A sample was withdrawn in order to record a $^1$H NMR spectrum for the determination of monomers' conversion. The polymer was precipitated by addition of 100 ml of water under stiffing in an ice bath. The polymer mass was isolated through vacuum filtration. The precipitated polymer was then dried under vacuum at 60° C. for 24 hours. The total monomer conversion was 97%. The inherent viscosity of this copolymer was 0.79 dL/g measured in chloroform at 25° C. The lactide/glycolide molar ratio determined by $^1$H NMR was 73:27. The weight averaged molecular weight was $8.92 \times 10^4$ Da with a polydispersity index of 1.6 as measured by gel permeation chromatography using THF as the mobile phase and polystyrene standards.

Example 4

In an 9 mL autoclave vial, 0.75 g D,L-lactide (0.0052 mol) and 0.188 g (0.0016 mol) Glycolide were placed under a continuous flow of argon, followed by the addition of 0.00063 g ($3.41 \times 10^{-6}$ mol) 1-dodecanol (solution in toluene) and 0.00028 g ($6.83 \times 10^{-7}$ mol) Sn(Oct)2 (solution in toluene). 4 mL of toluene was added to the autoclave vial under continuous flow of argon. The autoclave vial was then sealed under argon and immersed into a thermostated oil bath under stirring at 130° C. After 24 hours, the polymerization reaction was stopped by quenching (i.e., by placing the flask into an ice bath). 10 ml of acetone was added in the autoclave vial to dilute the produced viscous solution under stirring overnight. The diluted solution was transferred in a round bottom flask and evaporated to dryness. The residues were redissolved in 10 ml of acetone under stirring. A sample was withdrawn in order to record a $^1$H NMR spectrum for the determination of monomers' conversion. The polymer was precipitated by addition of 100 ml of water under stiffing in mass was isolated through vacuum filtration. The precipitated polymer was then dried under vacuum at 60° C. for 24 hours. The total monomer conversion was 96%. The inherent viscosity of this copolymer was 0.9 dL/g measured in chloroform at 25° C. The lactide/glycolide molar ratio determined by $^1$H NMR was 73:27. The produced polymer has a polydispersity index of 1.9 as measured by gel permeation chromatography using THF as the mobile phase and polystyrene standards.

Example 5

In an 9 mL autoclave vial, 0.90 g D,L-lactide (0.0062 mol) and 0.0805 g (0.694 mmol) Glycolide were placed under a continuous flow of argon, followed by the addition of 0.000646 g ($3.47 \times 10^{-6}$ mol) 1-dodecanol (solution in toluene) and 0.000281 g ($6.94 \times 10^{-7}$ mol) Sn(Oct)$_2$ (solution in toluene). 4 mL of toluene was added to the autoclave vial under continuous flow of argon. The autoclave vial was then sealed under argon and immersed into a thermostated oil bath under stirring at 130° C. After 24 hours, the polymerization reaction was stopped by quenching (i.e., by placing the flask into an ice bath). 10 ml of acetone was added in the autoclave vial to dilute the produced viscous solution under stirring overnight. The diluted solution was transferred in a round bottom flask and evaporated to dryness. The residues were redissolved in 10 ml of acetone under stirring. A sample was withdrawn in order to record a $^1$H NMR spectrum for the determination of monomers' conversion. The polymer was precipitated mass was isolated through vacuum filtration. The precipitated polymer was then dried under vacuum at 60° C. for 24 hours. The total monomer conversion was 98%. The inherent viscosity of this copolymer was 0.63 dL/g measured in chloroform at 25° C. The lactide/glycolide molar ratio determined by $^1$H NMR was 87:13. The weight averaged molecular weight was $5.47 \times 10^4$ Da with a polydispersity index of 2.5 as measured by gel permeation chromatography using THF as the mobile phase and polystyrene standards.

Example 6

In an 9 mL autoclave vial, 0.75 g D,L-lactide (0.0052 mol) and 0.188 g (0.0016 mol) Glycolide were placed under a continuous flow of argon, followed by the addition of 0.0018 g ($9.97 \times 10^{-6}$ mol) glucose (solution in toluene) and 0.00138 g ($3.41 \times 10^{-6}$ mol) Sn(Oct)$_2$ (solution in toluene). 4 mL of toluene was added to the autoclave vial under continuous flow of argon. The autoclave vial was then sealed under argon and immersed into a thermostated oil bath under stiffing at 130° C. After 24 hours, the polymerization reaction was stopped by quenching (i.e., by placing the flask into an ice bath). 10 ml of acetone was added in the autoclave vial to dilute the produced viscous solution under stirring overnight. The diluted solution was transferred in a round bottom flask and evaporated to dryness. The residues were redissolved in 10 ml of acetone under stirring. A sample was withdrawn in order to record a $^1$H NMR spectrum for the determination of monomers' conversion. The polymer was precipitated mass was isolated through vacuum filtration. The precipitated polymer was then dried under vacuum at 60° C. for 24 hours. The total monomer conversion was 98%. The inherent viscosity of this copolymer was 0.33 dL/g measured in chloroform at 25° C. The lactide/glycolide molar ratio determined by $^1$H NMR was 72:28.

The invention claimed is:

1. A method of polymerization of lactide and glycolide, comprising the step of performing polymerization under stirring, in the presence of an organic solvent, a metal catalyst and optionally a co-initiator, wherein the polymerization is performed in a closed sealed reactor system, which does not allow air or other gas exchange between an inner and an outer part of it once it is sealed.

2. A method according to claim 1, wherein the metal catalyst is selected from tin, zinc, aluminum catalysts.

3. A method according to claim 2, wherein the metal catalyst is selected from halides, alkoxides and carboxylic acid salts of tin, zinc and aluminum.

4. A method according to claim 3, wherein the metal catalyst is selected from tin and aluminum alkoxides and carboxylic acid salts.

5. A method according to claim 4, wherein the metal catalyst is selected from tin alkoxides and carboxylic acid salts.

6. A method according to claim 1, wherein the solvent is selected from aliphatic and aromatic hydrocarbons, halogenated aliphatic and aromatic hydrocarbons and aliphatic and aromatic ethers.

7. A method according to claim 1, wherein the ratio of he solvent with respect to the combined mass of the monomers is at least 1 ml per gram.

8. A method according to claim 1, wherein the Mw of the resulting polymer is at least $5 \times 10$ Da, as measured by GPC method.

9. A method according to claim 1, wherein the co-initiator is a mono-, di- or polyalcohol with 1-20 carbon atoms.

10. A method according to claim 1, wherein the polymer produced is linear.

11. A method according to claim 1, wherein the polymer produced is branched.

12. A method for producing a drug delivery system comprising an active pharmaceutical ingredient, said method comprising the step of producing a polymer with a method as defined in claim 1.

* * * * *